United States Patent
Tsuchino

(10) Patent No.: US 6,879,661 B2
(45) Date of Patent: Apr. 12, 2005

(54) RADIOGRAPHING APPARATUS INCLUDING A CONTROL SECTION FOR ESTABLISHING A STANDBY MODE IN A RADIOGRAPHING SECTION

(75) Inventor: Hisanori Tsuchino, Hino (JP)

(73) Assignee: Konica Corporation, Tokyo (JP)

( * ) Notice: Subject to any disclaimer, the term of this patent is extended or adjusted under 35 U.S.C. 154(b) by 67 days.

(21) Appl. No.: 10/091,254

(22) Filed: Mar. 4, 2002

(65) Prior Publication Data

US 2002/0131553 A1 Sep. 19, 2002

(30) Foreign Application Priority Data

Mar. 19, 2001 (JP) ........................................ 2001-078949
Mar. 19, 2001 (JP) ........................................ 2001-078950
Mar. 19, 2001 (JP) ........................................ 2001-078951

(51) Int. Cl.[7] .............................................. H05G 1/56
(52) U.S. Cl. ........................... 378/116; 378/91; 378/92; 378/114; 378/115; 378/117
(58) Field of Search ........................... 378/91, 92, 101, 378/114, 115, 116, 117, 118

(56) References Cited

U.S. PATENT DOCUMENTS

| | | | | |
|---|---|---|---|---|
| 4,037,107 A | * | 7/1977 | Lutz et al. ..................... 378/92 |
| 4,080,536 A | * | 3/1978 | Brehm et al. .................. 378/92 |
| 4,918,714 A | * | 4/1990 | Adamski et al. ............. 378/121 |
| 4,991,193 A | * | 2/1991 | Cecil et al. .................. 378/117 |
| 5,018,178 A | * | 5/1991 | Katsumata .................... 378/91 |
| 5,572,567 A | * | 11/1996 | Khutoryansky et al. .... 378/197 |
| 5,636,259 A | * | 6/1997 | Khutoryansky et al. .... 378/197 |
| 5,867,561 A | * | 2/1999 | Strasser et al. ............. 378/98.2 |
| 6,027,247 A | * | 2/2000 | Tachi et al. .................. 378/196 |
| 6,178,225 B1 | * | 1/2001 | Zur et al. ................... 378/98.2 |
| 6,285,742 B1 | * | 9/2001 | Haumann et al. ........... 378/116 |
| 6,359,961 B1 | * | 3/2002 | Aufrichtig et al. ............ 378/41 |
| 6,370,229 B1 | * | 4/2002 | Tsuchino et al. ........... 378/165 |
| 6,435,713 B1 | * | 8/2002 | Lizuka ....................... 378/195 |
| 6,501,827 B1 | * | 12/2002 | Takasawa ................... 378/116 |
| 6,614,873 B1 | * | 9/2003 | Taylor et al. ................. 378/62 |
| 6,707,880 B2 | * | 3/2004 | Yamayoshi .................. 378/92 |
| 2002/0080918 A1 | * | 6/2002 | Sako .......................... 378/115 |

* cited by examiner

*Primary Examiner*—Allen C. Ho
(74) *Attorney, Agent, or Firm*—Frishauf, Holtz, Goodman & Chick, P.C.

(57) ABSTRACT

A radiographing apparatus, is provided which includes a control section and a plurality of radiographing sections, each of which is connected to the control section. The control section establishes a standby mode in each of the radiography sections when each of the plurality of radiographing sections has been unused for a period of time which exceeds a predetermined time period.

8 Claims, 4 Drawing Sheets

RADIOGRAPHING APPARATUS INCLUDING A CONTROL SECTION FOR ESTABLISHING A STANDBY MODE IN A RADIOGRAPHING SECTION

BACKGROUND OF THE INVENTION

The present invention relates to a radiographing apparatus, and in particular, to a radiographing apparatus that can radiograph an image of an internal texture of the human body, by radiation emitted from a radiation emitting section.

For the purpose of inspecting disease or an injury, there is known a radiographing apparatus that radiographs the internal texture of a patient, using radiation such as X-ray. In such a radiographing apparatus, there is a radiographing apparatus wherein a standby mode is established automatically, when the apparatus is not employed for a certain time, from the view point of energy saving or life protection of consumable parts.

By the way, in a certain type of the radiographing apparatus, there is a case that one set of a control apparatus is used to control a plurality of radiographing sections. In this case, when standby mode is established on all the radiographing apparatus by the reason that one radiating section is not employed for a certain time period, the other radiographing section cannot be employed, though it is required to be employed, which is not preferable. However, the standby mode should be established in the radiating section which is not employed for a long time, which is preferable from the view point of energy saving.

Further, there is a problem of timing for canceling the standby mode. For example, it is troublesome that an operator must perform special operations, in order to cancel the standby mode. Further, it is wasteful that the standby modes are canceled indiscriminately, even when there is no need to cancel the standby mode.

The invention has been achieved in view of the above-mentioned problems of the conventional art, and a first object of the invention is to provide a radiographing apparatus wherein a standby mode is established or canceled appropriately.

Incidentally, talking about the radiographing apparatus, there are many cases that the radiographing apparatus is installed in a radiographing room wherein the radiation emitting section is installed, and that an operating section by which the radiographing apparatus is operated is installed in an operating room separated from the radiographing room.

A radiologist who radiographs a patient by using the radiographing apparatus establishes radiographing conditions in the operating room at first, then the radiologist guides the patient to the radiographing apparatus in the radiographing room, and at last, the radiologist returns to the operating room to radiograph the patient. However, there sometimes is a case that the radiographing condition for the patient should be changed, when the radiologist checks again the patient in the radiographing room after establishing the radiographing condition in the operating room. The establishment or the change of the radiographing condition is only performed in the operating room in the conventional technology. In that case, the radiologist must go back to the operating room to change the radiographing condition, because the establishment or the change of the radiographing condition is only performed in the operating room. During that period, however, the patient may sometimes move from the radiographing position, and it may cause a fear that the radiologist must go back to the radiographing room to guide the patient again.

The second object of the invention is to provide a radiographing apparatus which is easier to operate.

SUMMARY OF THE INVENTION

The first object of the invention can be achieved by the following structures.

(1) In a radiographing apparatus of the invention, having therein a control apparatus and a plurality of radiographing sections each being connected to the control apparatus, the control apparatus establishes the standby mode for each of the plurality of radiographing sections, in accordance with the fact that the non using time for each radiographing section exceeds the prescribed time, for example, the radiographing section being not employed plans the energy saving or the prolongation of the life of the consumable parts such as CRT, by establishing the standby mode, and the radiographing section which is employed or has high possibility of being employed does not establish the standby mode, and the control apparatus can perform radiographing quickly.

(2) Further, the control apparatus determines the prescribed times for each radiographing section respectively in accordance with frequency in use of each radiographing section. For example, the prescribed time for the radiographing section whose frequency in use is high is established to be long, accordingly standby mode is hard to be established, and radiographing is performed quickly, on the other hand, the prescribed time for the radiographing section whose frequency in use is low is established to be short, accordingly standby mode is easy to be established, and it can be planed to save the energy or to prolong the life of the consumable parts such as CRT.

(3) Still further, it is preferable that the standby mode is established in the control apparatus, after the standby modes have been established in all the plurality of radiographing sections, but it is also acceptable that the standby mode is established in the control section at the same time when the standby mode is established in the final radiographing section.

(4) In the radiographing apparatus wherein the standby mode is established when the radiographing apparatus is not employed for the prescribed time, there is provided the control apparatus which cancells the standby mode when a radiographing order is inputted via a network. Therefore, when the radiographing order is inputted via the network, for example, it is judged to radiograph at once, and the radiographing apparatus can radiograph quickly by canceling the standby mode through the control apparatus.

(5) Still further, when the standby mode explained above is canceled when the control apparatus is connected to the radiographing section, a useless canceling is suppressed, which is preferable.

(6) Still further, when the control apparatus is connected to a plurality of radiographing sections and the radiographing order is inputted to the specific radiographing section, if the standby mode is cancelled only for the specific radiographing section, the useless canceling is suppressed, which is preferable.

(7) Still further, in the radiographing apparatus wherein the standby mode is established when the radiographing apparatus is not employed for the prescribed time period, when the standby modes are established in the control apparatus and a plurality of radiographing sections which are connected to the control apparatus, the standby mode of the control apparatus is canceled by the operation of the control apparatus before the standby mode of the radiographing section is cancelled in the radiographing apparatus of the invention, and the radiographing section can be selected through the control apparatus.

Therefore, it is possible to select the radiographing section through the control apparatus, for example, and thereby to conduct preparation for radiographing including the standby mode, thus, the standby mode can be canceled only for the required radiographing section, which is preferable.

(8) Still further, in the radiographing apparatus wherein the standby mode is established when the radiographing apparatus is not operated for the prescribed time period, when the standby mode is established in the control apparatus and the radiation emitting section which is connected to the control apparatus, if the control apparatus cancels the standby mode when the radiographing apparatus is operated, the control section cancels the standby mode to perform the radiographing quickly, when the radiation emitting section, for example, is operated, because it is judged that the radiographing is performed at once.

(9) Still further, in the radiographing apparatus wherein the standby mode is established when the radiographing apparatus is not operated for the prescribed time period, when the radiation emitting section is corresponded with the specific radiographing section, under the condition that the standby modes are established in the control apparatus and a plurality of radiographing sections which are connected to the control apparatus, the control apparatus cancels the standby mode for the specific radiographing section having the correspondence, thus, it is possible to cancel the standby mode only for the requested radiographing section, which is preferable.

(10) Still further, in the radiographing apparatus wherein the standby mode is established when the radiographing apparatus is not employed for the prescribed time period, when the standby modes are established in the control apparatus and a plurality of radiographing sections which are connected to the control apparatus, the control section is made to cancel the standby mode for all the plurality of radiographing sections having correspondence, when the radiation emitting section is made correspondence with each radiographing section, it is possible to cancel the standby mode only for the requested radiographing section, which is preferable.

The second object can be achieved by the following structures.

(11) Since the radiographing apparatus of the invention is provided with the radiographing section which forms an image corresponding to the radiation received from the radiation emitting section, a first operating section which is connected to the radiographing section and establishes the radiographing condition of the radiographing section, and a second operating section which changes the radiographing condition established through the first operating section, even when the first operating section is installed in the operating room that is away from the radiographing section, the operator can change the radiographing condition, without going back to the operating room, by installing the second operating section in the radiographing room, and by operating the second operating section, accordingly, the operator can radiograph the patient quickly, which is very convenient.

(12) Still further, it is preferable if the radiographing section is connected to the first operating section via the network.

(13) Still further, it is preferable if the second operating section is installed on the radiographing section detachably, because the operator can carry and use it in the radiographing room.

(14) Still further, the second operating section is provided with a communication means by which the operator can communicate with the first operating section via radio, and if the operator can transfer information about the change of the radiographing condition via the communication means, the operator can carry without being disturbed by a wiring, and which makes the operation to be easy.

(15) Still further, since the second operating section is provided with a display means which can display information about the radiographing condition established by the first operating section, the operator can change the radiographing condition, by watching the display on the display means.

(16) Still further, since the first operating section is provided with a display means which can display information about the radiographing condition changed by the second operating section, the operator can confirm the changed radiographing condition, by watching the display on the display means.

(17) Still further, if a priority is given to the operation of the second operating section rather than to that of the first operating section, the invention can avoid the problem that the radiographing condition cannot be changed by the operation of the second operating section.

(18) Still further, when the operator tries the change of the radiographing condition which cannot be performed on the second operating section, the operator can learn the impossibility of the change at once, by watching the display on the display means, since there is provided a display means which displays information about an impossibility of the change, which is preferable.

(19) Still further, in the radiographing apparatus, wherein the standby mode is established automatically, when the radiographing apparatus has not be employed for the prescribed time period, when the standby mode is canceled by the operation of the second operating section, the standby mode can be canceled by operating the second operating section, even though the standby mode is established to cover the long time of guiding the patient in the radiographing room and the operator can go to the operating room to radiograph the patient at once, which can suppress that the patient waits for a long time.

(20) Still further, if the second operating section is provided with a display means which displays information about the fact that the standby mode has been established, the operator can learn at a glance, whether it is in the standby mode or not, which is very convenient.

DETAILED DESCRIPTION OF THE PREFERRED EMBODIMENTS

Figure 1:
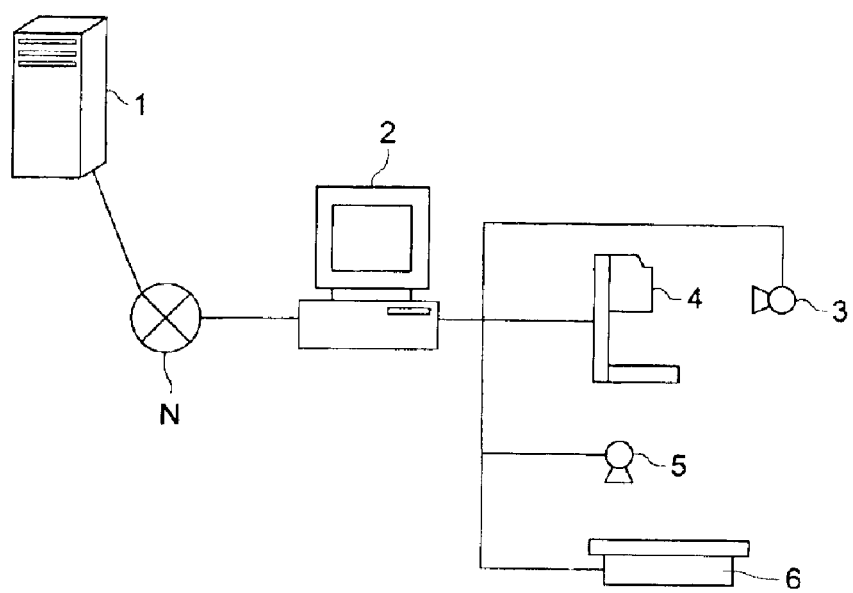
FIG. 1 is a schematic structural drawing of a network system including the radiographing apparatus of the embodiment.

The embodiments of the invention are explained as follows, referring to the drawings. FIG. 1 is a schematic structural drawing of a network system including the radiographing apparatus of the embodiment.

In FIG. 1, server 1 and control apparatus 2 which are connected each other by network N in a hospital construct a part of a network system. The control apparatus 2 is connected to first radiation emitting section 3, first radiographing section 4 which is corresponding to the first radiation emitting section 3, second radiation emitting section 5, and second radiographing section 6 which is corresponding to the second radiation emitting section 5 respectively, and it constitutes the radiographing apparatus together with them.

In the first radiographing section 4 and the second radiographing section 6, though there are provided transfer devices which transfer a radiographic image to digital image data, which, however are known so well that detailed explanations are omitted. Incidentally, instead of the transfer device, the customary X-ray films can be arranged in the plurality of radiographing sections 4 and 6.

Next, the working of the embodiment is explained. In order to save energy and to prolong the life of the display, the standby mode is established automatically in the radiographing apparatus of the embodiment, when the radiographing apparatus is not employed for a prescribed time period, and a main power supply and CRT display are cut. Incidentally, during the standby mode, a main CPU (not illustrated) stops running, but a sub-CPU (not illustrated) does not stop running, in the control apparatus 2.

Here, the control apparatus 2 can count and store the working time and frequency in use of the plurality of radiographing sections 4 and 6. Here, it is assumed that the radiographing section 4 has relatively high frequency in use, while the radiographing section 6 has relatively low frequency in use. Therefore, for the radiographing section 4 which has high frequency in use, the control apparatus 2 establishes a non-employment time (the prescribed time) for which the standby mode is established to be longer, for example 30 minutes, while for the radiographing section 6 which has low frequency in use, a non-employment time (the prescribed time) for which the standby mode is established is established to be shorter, for example 15 minutes.

That is, according to the embodiment, the control apparatus 2 establishes the standby mode for each of the plurality of radiographing sections 4 and 6 respectively when the non-employment time of each of the plurality of radiographing sections 4 and 6 exceeds the prescribed time determined respectively. Therefore, by establishing the standby mode to be shorter for the radiographing section 6 which has high possibility of non-employment, energy saving and the prolongation of the life of CRT can be attained, while for the radiographing section 4 which is employed or has high possibility of employment, the quick radiographing is made possible by establishing no standby mode.

However, the control apparatus 2 can make use of frequency in use for the determination of the prescribed time. For example, when the operator judges that frequency in use of the radiographing section 6 was low on yesterday but high on today, the operator can change the prescribed time of the radiographing section 6 to be longer (for example, to change from 15 minutes to 30 minutes) by the control apparatus 2.

Additionally, the control apparatus 2 can change the prescribed time according to the schedule of one week. In hospital, there is a case that day of the week on which the doctor takes charge is decided, for example, it is imaginable that the prescribed time of the radiographing section 4 is established to be longer for the day when a physician takes charge, while the prescribed time of the radiographing section 6 is established to be longer for the day when a surgeon takes charge. Further, it is preferable that the prescribed times for both of radiographing sections 4 and 6 are established to be shorter for the days such as Sunday or the national holidays when hospital is closed.

Incidentally, since the control apparatus 2 has a function to control the plurality of radiographing sections 4 and 6, it is preferable that the standby mode is established after the passage of the prescribed time, from establishment of the standby modes for both of the plurality of radiographing sections 4 and 6. However, when the control apparatus 2 is not used except for the plurality of radiographing sections 4 and 6, the standby mode may be established on the control section 2, at the moment when the standby mode is established on the final radiographing section.

Next, at the time of the standby mode set above, since information about the reservation of the radiographing is inputted in the server 1 which is installed in an office of the hospital, for example, it is possible to send information timely to the control apparatus 2 which is arranged at the radiographing room.

However, in the radiographing apparatus wherein the standby mode has been established, when the radiographing order is inputted from the server 1 via the network N, the sub-CPU respond to it and cancels the standby mode, and consequently it becomes possible to prepare the radiographing at once. However, when the control apparatus 2 is not connected to the plurality of radiographing sections 4 and 6, it is impossible to radiograph at once, even though the standby mode is canceled. Accordingly, the standby mode can be canceled only when the control apparatus 2 has been connected to the plurality of radiographing sections 4 and 6.

There is a case that information designating a radiographing section is included in a radiographing order inputted from the server 1, for example, the radiographing section 4 is designated for the radiographing of a chest which can be taken while standing. In that case, in the radiographing apparatus wherein the standby mode has been established, when such a radiographing order is inputted from the server 1 via the network N, the sub-CPU in the control apparatus 2 starts the main CPU, then the main CPU reads the designation of radiographing section included in the radiographing order, and the standby mode is canceled only for the radiographing section 4 (or 6) which has been read.

Further, as an example of a variation, in the radiographing apparatus wherein the standby mode has been established, when a radiographing order is inputted from the server 1 via the network N, the sub-CPU in the control apparatus 2 starts the main CPU, then, the operator can designate one of the plurality of radiographing sections 4 and 6 from the control apparatus 2 to cancel the standby mode. By the example mentioned above, the standby mode still exists without a break in the radiographing section not employed, which avoids waste.

Still further, in the case that the first radiation emitting section 3 is operated, it is judged that radiographing by the use of the first radiographing section 4 is performed, and in this case, it is preferable that the standby modes of the control apparatus 2 and the first radiographing section 4 are canceled. In the case that the second radiation emitting section 5 is operated, it is judged that radiographing by the use of the second radiographing section 6 is performed, and in this case, it is preferable that the standby modes of the control apparatus 2 and the second radiographing section 6 are canceled.

Still further, it may be possible that, the radiation emitting sections 3 and 5 and radiographing sections 4 and 6 are not corresponded each other in the control apparatus 2, and in this case, the control apparatus 2, by itself, can make the first radiation emitting section 3 and the second radiographing section 6 to correspond each other. In this case, it is possible to cancel the established standby mode for the second radiographing section 6, responding to the fact that the control apparatus 2 made the first radiation emitting section 3 and the second radiographing section 6 to correspond each other. It is also possible to cancel the established standby modes for all the apparatuses, responding to the fact that the control apparatus 2 made the first radiation emitting section 3 and the second radiographing section 6 to correspond each other, and the fact that the control apparatus 2 made the second radiation emitting section 5 and the first radiographing section 4 to correspond each other.

Figure 2:
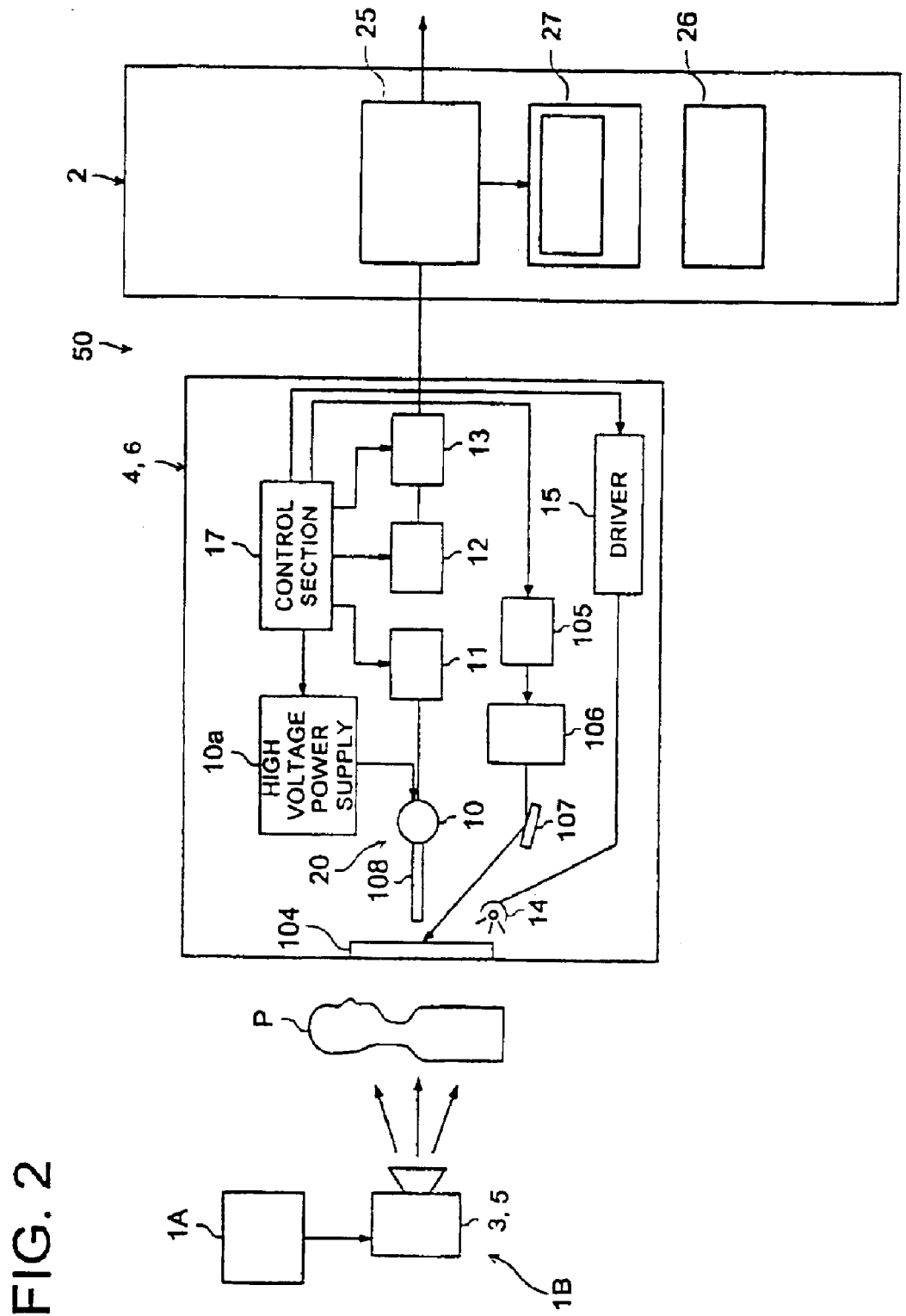
FIG. 2 is a drawing showing a schematic structure of the radiographing apparatus of the embodiment.

FIG. 2 is a drawing showing a schematic structure of the radiographing apparatus of the embodiment. As shown in FIG. 2, radiographing apparatus 50 is provided with radiographing sections 4 and 6, and control apparatus (controller) 2 though the supporting pillar 33 is not illustrated. Besides, the hand carry controller 36 is not illustrated.

In each of the plurality of radiographing sections 4 and 6, radiographic image (X-ray transmitted plane image) information of the subject, such as human body on which X-ray from X-ray emitting apparatus 1B has been irradiated, is accumulated and recorded successively in plate-shaped stimulable phosphor plate 104 temporarily, and next, the stimulable phosphor plate 104 is scanned by the laser beam to emit stimulated light, and then, is read photo-electrically in sequence by the photoelectric reading section 20 to be stored as image signal. Incidentally, the stimulable phosphor plate 104 is the one wherein storage-type phosphor substances are multi-layered on a support. When X-ray from each of X-ray sources (radiation emitting section) 3 and 5 driven by drive source 1A is irradiated on the stimulable phosphor plate 104, a part of X-ray energy is accumulated on a storage-type phosphor. Further, when exciting light such as visible light or laser beam is irradiated, a stimulable phosphor emits stimulated light in accordance with the accumulated X-ray energy. Then, each of the plurality of radiographing sections 4 and 6 emits erasing light to the stimulable phosphor plate 104 from which the image signals have been read, and makes X-ray energy remaining on the plate to be ejected from the plate 104, to be ready for the next radiographing.

Each of the plurality of radiographing sections 4 and 6 is provided with stimulable phosphor plate 104 on which radiographic image information of subject P is accumulated, laser light source section 106 composed of a laser diode which generates a laser beam as exciting light for stimulable phosphor plate 104, laser driving circuit 105 to drive the laser light source section 106, optical system 107 to lead the laser light beam from the laser light source section 106 to the stimulable phosphor plate 104 for scanning, and photoelectric reading section 20 which converges stimulable phosphor excited by an exciting laser beam, and performs photoelectric conversion to obtain an image signal. The photoelectric reading section 20 is provided with light converging body 108 which converges stimulable phosphor excited by the exciting laser beam, photomultiplier 10 which performs photoelectric conversion of light converged by converging body 108, high voltage power supply 10a which applies voltage to the photomultiplier 10, conversion section 11 which converts a current signal from the photomultiplier 10 to a digital signal by current-voltage conversion, voltage amplification, and A/D conversion, correcting section 12 which corrects the digital signal converted by the conversion section 11, and image transmitting section 13 which transmits the digital signal corrected by the correcting section 12, and further, transmits the digital signal of radiographic image information read and obtained to controller 2. Incidentally, the correcting section 12 is composed of a RISC processor to correct a delay of response and an unevenness of the digital signal.

Further, in order to eliminate X-ray energy remaining on the stimulable phosphor plate 104 from which an image has been read, the plurality of radiographing sections 4 and 6 are provided with halogen lamp 14 which emits erasing light and driver 15 to drive the halogen lamp 14. Further, each of the plurality of radiographing sections 4 and 6 is provided with control section 17 which controls laser driving circuit 105, high voltage power supply 10a, conversion section 11, correcting section 12, image transmitting section 13, and driver 15.

Further, the laser light source section 106, the optical system 107, converging body 108, photomultiplier 10, and halogen lamp 14 in the plurality of radiographing sections 4 and 6, which integrally move as an unillustrated sub scanning unit in a sub scanning direction perpendicular to the laser scanning direction, through an unillustrated ball-screw mechanism.

The sub scanning unit moves to perform sub-scanning during image reading, and makes the halogen lamp 14 to light to erase the remaining X-ray energy while moving backward.

The control apparatus 2 is provided with personal computer main body section 25, key board 26 and monitor display section 27, and stores the digital signal of radiographic image information received from the plurality of radiographing sections 4 and 6 in a memory temporarily, then performs image processing, and controls the display onto the monitor display 27 and image processing in accordance with an operating input from the key board 26, to output radiographic image information which has been subjected to image processing.

As mentioned above, the invention has been explained referring to the embodiments, but the invention should not be interpreted by limiting to the above-mentioned embodiments, and needless to say, it is possible to modify and to improve the embodiments appropriately. For example it is possible to provide three or more radiographing sections.

The invention makes it possible to provide the radiographing apparatus, wherein the standby mode can be established and canceled appropriately.

Figure 3:
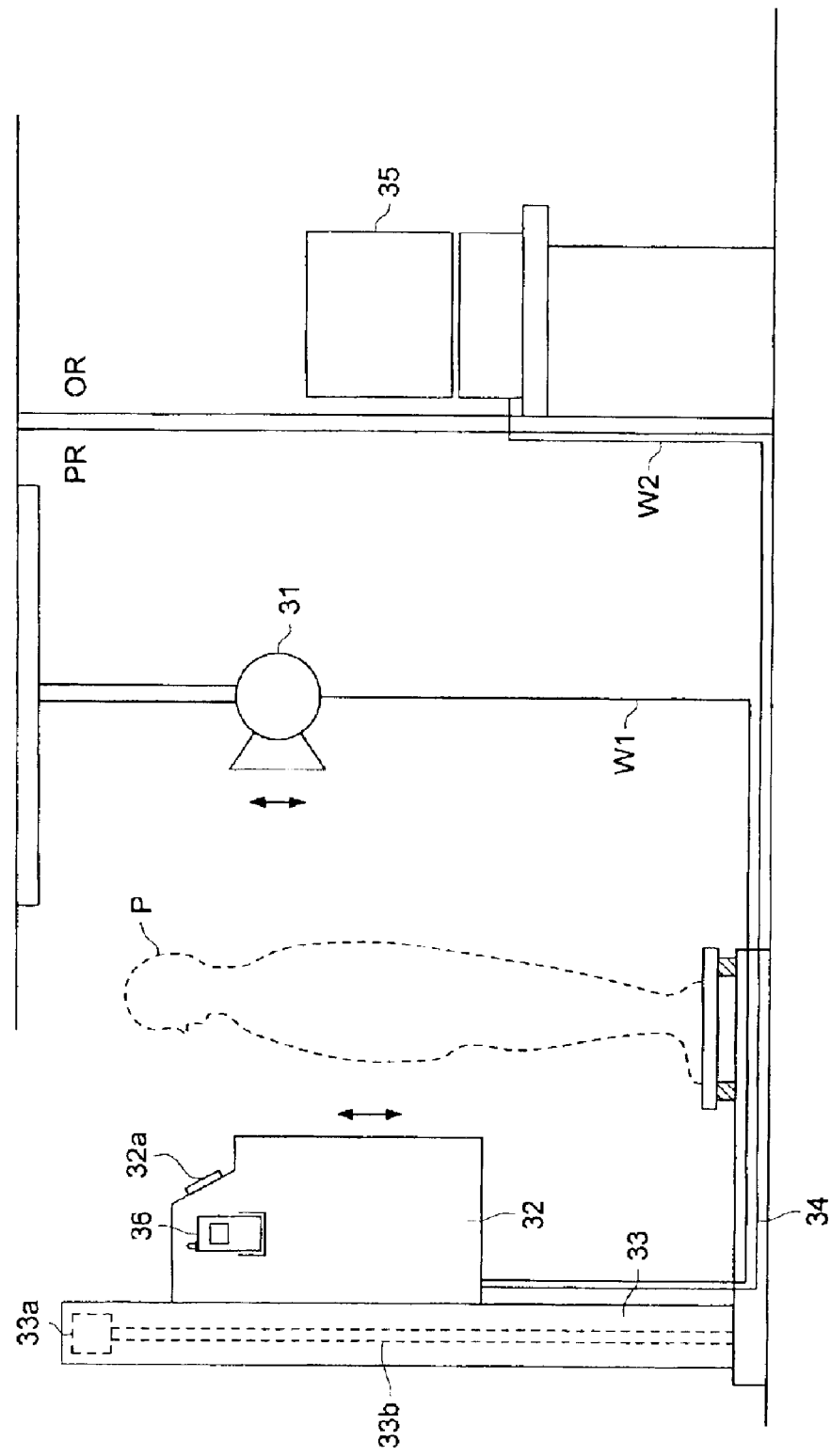
FIG. 3 is a schematic drawing of the radiographing apparatus of the embodiment.

FIG. 3 is a schematic structural drawing of the radiograph apparatus of the embodiment.

As shown in FIG. 3, the radiographing apparatus of the embodiment is composed of radiation emitting section 31 hung from the ceiling of radiographing room PR, radiographing section 32 connected to radiation emitting section 31 via wiring W1 and arranged in the radiographing room PR to face the radiation emitting section 31, supporting pillar 33 supporting the radiographing section 32 to move up and down freely, support plate 34 supporting the supporting pillar 33 vertically, controller 35 representing the first operating section arranged in operating room OR and connected to the radiographing section 32 via wiring W2, and hand carry controller 36 representing the second operating section provided on the radiographing section 32 detachably.

Motor 33a and screw shaft 33b coupled to the rotation shaft of the motor 33a are installed inside the supporting pillar 33. When the motor 33a is driven by the signal from the unillustrated CPU, the screw shaft 33b rotates to make the radiographing section 32 to go up and down.

A conversion device which converts the radiation image into the digital image is built in the radiographing section 32. However, the device itself is known so the details thereof are not described below. Incidentally, conventional X-ray film can be arranged in the radiographing section 32, instead of the conversion device.

There is arranged the display 32a which makes it possible to observe person P be radiographed, on the front of the radiographing section 32 (on the right side in FIG. 3).

Figure 4:
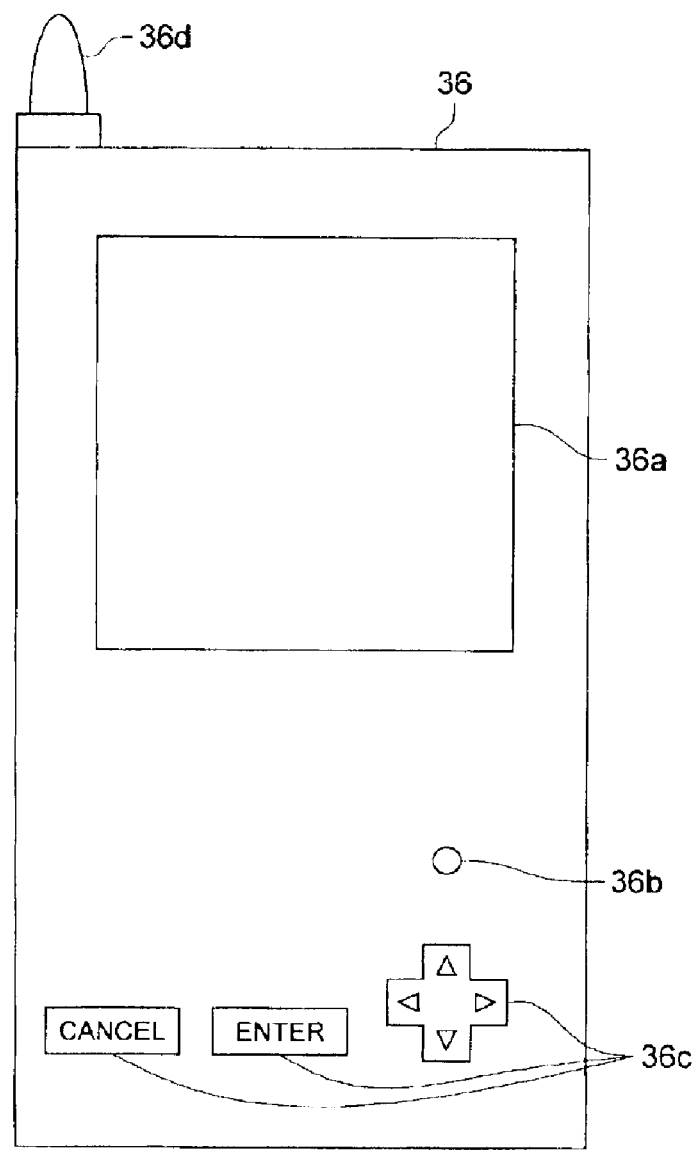
FIG. 4 is an enlarged drawing of a hand carry controller.

FIG. 4 is an enlarged drawing of the hand carry controller 36. In FIG. 4, the hand carry controller is provided with liquid crystal screen 36a representing a display means, LED 36b, operation switch 36c and communication device 36d representing a wireless communicating means.

Next, operations in the embodiment of the invention will be explained. The radiographing section 32 and controller 35 are connected to an external apparatus (not illustrated) via the network, and information about radiographing (a radiographing order) is sent from the external apparatus. The operator such as a radiologist determines the radiographing condition of the subject P such as a patient in the operating room OR by the controller 35 based on the information.

Then, the operator enters the radiographing room PR to guide the subject P to supporting plate 34, and makes radiation emitting section 31 and radiographing section 32 to go up and down to obtain the best position for the subject P, by pushing an unillustrated elevating button.

At this time, there is a case that the operator wants to change the radiographing condition which was established on an earlier occasion. However, if the operator returns to the operating room OR to re-establish the radiographing condition, it takes time and it keeps the subject P waiting.

In the case of the embodiment, in that case, the operator can change the radiographing condition, by using operation switches 36c of the hand carry controller 36. More concretely, the radiographing condition (information such as an exposure dose) established by the controller 35 is inputted in the hand carry controller 36 via the communication device 36d wirelessly, and is displayed on the liquid crystal screen 36a, so that the operator can reverse the display of the condition which the operator wants to change and can replace them with the new numerical values, by operating operation switch 36c while watching the liquid crystal screen 36a. The changed condition is inputted in the controller 35 via communication device 36d wirelessly, and the established radiographing condition can be rewritten.

In the embodiment mentioned above, the operator can change the radiographing condition by the hand carry controller 36, without going back to the operating room OR to operate the controller 35, accordingly, the operator can radiograph the subject P quickly, without making the subject P waiting, which is very convenient.

Further, if the hand carry controller 36 is installed on the radiographing section detachably, the operator can carry it in the radiographing room, while guiding the subject P, which is preferable. Since the correspondence of information is performed between the hand carry controller 36 and the controller 35 via the wireless method, there is no case that the operator is troubled by the wiring, which makes operations to be easier.

Incidentally, when a priority is given to the operation of the hand carry controller 36 rather than to the operation of the controller 35, it is possible to avoid a problem that the radiographing condition is not changed in spite of the operation of the hand carry controller 36. However, it is also possible to arrange so that a priority to be given to the operation of the hand carry controller 36 or to the operation of the controller 35 can be changed by setting.

In order to prevent the confusion, there is a preferable case that the operator cannot change the distinguish number of the subject P, for example, and for such case, it is considered that the display of the non-changeable radiographing condition is not reversed on the liquid crystal screen 36a, and the operator can learn at once that the operator cannot change, by watching the screen, which is preferable.

Incidentally, in the radiographing apparatus of the embodiment, the standby mode which cuts a supply of the main power source is automatically established, when the radiographing apparatus is not used for the prescribed time period (including the continuous non-operation), and the standby mode can be cancelled by touching the operating switch 36c of the hand carry controller 36. Accordingly, though the standby mode is established to cover the long time for guiding the subject P in the radiographing room PR, it can be cancelled by the operation of the operating switch 36c of the hand carry controller 36, and after that, the operator goes to the operating room OR, then the operator can perform the radiographing, without keeping the subject P waiting.

Further, if the hand carry controller 36 is provided with a display means (for example, lighting or blinking of LED 36b) which displays information showing that the standby mode has been established, it is quite obvious for the operator whether it is in the standby mode or not, which is very convenient.

As stated above, the embodiment of the present invention has been explained. However, the present invention is not limited to the above embodiment. The above embodiment may be modified, changed or improved within the scope of the present invention.

The invention makes it possible to provide the radiographing apparatus, wherein the operation is easy for the operator.

What is claimed is:

1. A radiographing apparatus, comprising:
   a radiographing section, having a normal mode and a standby mode, for radiographing a patient to obtain a medical image of the patient in the normal mode;
   an irradiating section for irradiating radiation to the radiographing section; and
   a control section for controlling the radiographing section;
   wherein under a condition that the radiographing section is in the standby mode, when the irradiating section is operated, the control section cancels the standby mode in accordance with the operation of the irradiating section and puts the radiographing section in the normal mode.

2. The radiographing apparatus of claim 1, further comprising:
   a plurality of radiographing sections; and
   a plurality of irradiating sections each correlated with one of the plurality of radiographing sections;
   wherein when one of the irradiating sections is operated, the control section cancels the standby mode of the correlated radiographing section in accordance with the operation of said irradiating section and puts the correlated radiographing section in the normal mode.

3. The radiographing apparatus of claim 1, further comprising:
a plurality of radiographing sections; and
a plurality of irradiating sections;
wherein when one of the irradiating sections is operated, the control section correlates said irradiating section with one of the plurality of radiographing sections, cancels the standby mode of the correlated radiographing section in accordance with the operation said irradiating section, and puts the correlated radiographing section in the normal mode.

4. The radiographing apparatus of claim 1, wherein when the radiographing section does not conduct a radiographing operation for a predetermined time period, the radiographing section enters the standby mode.

5. A radiographing apparatus, comprising;
a radiographing section, having a normal mode and a standby mode, for radiographing a patient to obtain a medical image of the patient; and
a control section, connected to a network so as to receive a radiographing order, for controlling the radiographing section;
wherein when the radiographing section is in the standby mode, the control section cancels the standby mode in accordance with the radiographing order received through the network and puts the radiographing section in the normal mode.

6. The radiographing apparatus of claim 5, comprising a plurality of radiographing sections;
wherein when the control section receives a radiographing order for a specific radiographing section among the plurality of radiographing sections through the network, the control section cancels only the standby mode of the specific radiographing section in accordance with the radiographing order and puts the specific radiographing section in the normal mode.

7. The radiographing apparatus of claim 5, wherein when the radiographing section does not conduct a radiographing operation for a predetermined time period, the radiographing section enters the standby mode.

8. The radiographing apparatus of claim 5, wherein the control section receives the radiographing order through the network from a server installed in a hospital.

* * * * *